(12) United States Patent
Muniz

(10) Patent No.: US 11,103,184 B2
(45) Date of Patent: *Aug. 31, 2021

(54) WEARABLE ELECTROENCEPHALOGRAPHY DEVICE AND METHODS OF USE THEREOF

(71) Applicant: Carlos Federico Muniz, Baltimmore, MD (US)

(72) Inventor: Carlos Federico Muniz, Baltimmore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/509,887

(22) Filed: Jul. 12, 2019

(65) Prior Publication Data

US 2019/0328326 A1  Oct. 31, 2019

Related U.S. Application Data

(63) Continuation of application No. 14/510,110, filed on Oct. 8, 2014, now Pat. No. 10,349,888.

(51) Int. Cl.
*A61B 5/00* (2006.01)
*A61B 5/291* (2021.01)

(52) U.S. Cl.
CPC ............ *A61B 5/6806* (2013.01); *A61B 5/291* (2021.01); *A61B 5/0006* (2013.01); *A61B 5/4094* (2013.01); *A61B 2562/0209* (2013.01); *A61B 2562/125* (2013.01); *A61B 2562/222* (2013.01)

(58) Field of Classification Search
CPC ................. A61B 5/6806; A61B 5/0478; A61B 2562/222; A61B 2562/0209; A61B 5/0006; A61B 2562/125; A61B 5/4094
See application file for complete search history.

(56) References Cited

U.S. PATENT DOCUMENTS

| 4,144,877 | A | 3/1979 | Frei et al. |
| 4,279,258 | A | 7/1981 | John |
| 4,323,076 | A | 4/1982 | Sams |
| 4,395,820 | A | 8/1983 | Sams |
| 4,411,273 | A | 10/1983 | John |
| 4,417,592 | A | 11/1983 | John |
| 4,488,726 | A | 12/1984 | Murray |
| 4,510,939 | A | 4/1985 | Brennan et al. |
| 4,537,198 | A | 8/1985 | Corbett |
| 4,709,702 | A | 12/1987 | Sherwin |
| 5,357,957 | A | 10/1994 | Itil et al. |
| 6,052,619 | A * | 4/2000 | John ................... A61B 5/0476 600/544 |
| 6,201,982 | B1 | 3/2001 | Menkes et al. |

(Continued)

OTHER PUBLICATIONS

S. R. Sinha, et al., "American Clinical Neurophysiology Society Guideline 1: Minimum Technical Requirements for Performing Clinical Electroencephalography", Journal of Clinical Neurophysiology, Aug. 2016, p. 303-307, vol. 33, Issue 4.

(Continued)

*Primary Examiner* — Rex R Holmes

(57) ABSTRACT

The invention provided herein relates to a wearable medical device and methods of use thereof for monitoring brain signals by electroencephalography technology in critically ill subjects suspected of having abnormal brain wave patterns including but not limited to electrographic seizures, spike and waves, periodic discharges and rhythmic delta activity.

14 Claims, 16 Drawing Sheets

(56) References Cited

U.S. PATENT DOCUMENTS

| | | | |
|---|---|---|---|
| 6,567,990 | B1 | 5/2003 | Spitznagle |
| 6,574,513 | B1 | 6/2003 | Collura et al. |
| 6,640,122 | B2 | 10/2003 | Manoli et al. |
| 7,551,952 | B2 | 6/2009 | Gevins et al. |
| 8,694,084 | B2 | 4/2014 | Sullivan |
| 8,948,849 | B2 | 2/2015 | Diamond |
| 8,989,835 | B2 | 3/2015 | Badower |
| 9,408,575 | B2 | 8/2016 | Bordoley et al. |
| 9,622,702 | B2 | 4/2017 | Badower |
| 10,349,888 | B2 * | 7/2019 | Muniz .................. A61B 5/6806 |
| 2004/0267145 | A1 * | 12/2004 | David .................. A61B 5/6822 600/509 |
| 2008/0300488 | A1 | 12/2008 | Schutz et al. |
| 2010/0111763 | A1 | 5/2010 | Kahn et al. |
| 2011/0218436 | A1 | 9/2011 | Dewey et al. |
| 2011/0282231 | A1 | 11/2011 | Pradeep |
| 2011/0302694 | A1 | 12/2011 | Wang et al. |
| 2012/0029399 | A1 | 2/2012 | Sankai |
| 2012/0083710 | A1 | 4/2012 | Yarden |
| 2012/0287041 | A1 | 11/2012 | Bucholz |
| 2013/0127708 | A1 | 5/2013 | Jung |
| 2013/0158365 | A1 | 6/2013 | Chey et al. |
| 2014/0249436 | A1 | 9/2014 | Kabakov et al. |
| 2015/0296111 | A1 | 10/2015 | Rajan et al. |
| 2015/0342521 | A1 | 12/2015 | Narita et al. |
| 2016/0256111 | A1 | 9/2016 | Cheng |
| 2016/0287165 | A1 | 10/2016 | Abreu |
| 2017/0000369 | A1 | 1/2017 | Hyde et al. |

OTHER PUBLICATIONS

J. N. Acharya, et al., "American Clinical Neurophysiology Society Guideline 2: Guidelines for Standard Electrode Position Nomenclature", Journal of Clinical Neurophysiology, Aug. 2016, p. 308-311, vol. 33, Issue 4.

G. H. Klem et al., "The ten-twenty electrode system of the International Federation", Recommendations for the Practice of Clinical Neurophysiology: Guidelines of the International Federation of Clinical Physiology (EEG Suppl. 52), 1999, p. 3-6, Published by Elsevier Science B.V.

\* cited by examiner

WEARABLE ELECTROENCEPHALOGRAPHY DEVICE AND METHODS OF USE THEREOF

CROSS REFERENCE TO RELATED APPLICATIONS

This application claims priority to and the benefit of the prior filed, co-pending, and commonly owned patent application filed in the United States Patent and Trademark Office (USPTO) on Oct. 8, 2014, entitled "Wearable Electroencephalography Device and Methods of Use Thereof", assigned Ser. No. 14/510,110 ("the '110 application"), which pending application set to issue as U.S. Pat. No. 10,439,888 on Jul. 16, 2019, and which is incorporated by reference in its entirety.

The '110 application claimed priority to and benefit of the prior filed, then co-pending and commonly owned patent application filed in the USPTO on Oct. 8, 2013, entitled "Wearable Electroencephalography Device and Methods of Use Thereof", assigned Ser. No. 61/888,000, which is hereby incorporated by reference herein in its entirety.

FIELD OF THE INVENTION

The invention provided herein relates to a wearable mobile medical device and methods of use thereof for monitoring brain signals by electroencephalography technology in critically ill subjects suspected of having abnormal brain wave patterns including but not limited to electrographic seizures, spike and waves, periodic discharges and rhythmic delta activity.

BACKGROUND OF THE INVENTION

Approximately 11% of people in the United States will have a seizure during their lifetime. Of over 100 million yearly emergency visits in the United States, 1% of adult emergency department visits and 2% of children emergency department visits are due to seizures and up to 10% of these patients may be in status epilepticus—continuous prolonged seizures with ensuing brain damage and up to 20% mortality.

Similarly, over 4 million patients are admitted every year in critical condition to intensive care units in the United States. It has been estimated that up to 34% of these critically ill patients may be in a state termed non-convulsive status epilepticus, which carries high mortality. Non-convulsive status epilepticus is a medical emergency seen in up to 34% of critically ill and comatose patients in which large numbers of brain cells start to discharge in a hypersynchronous fashion and for prolonged periods of time, leading to brain damage. This condition requires emergency management with antiseizure medications and anesthetics.

Non-convulsive status epilepticus differs from convulsive status epilepticus in that it is practically impossible to ascertain the ongoing presence of seizures because the patient does not present with clinically visible evidence. In the latter case, the patient may have continuous rhythmic jerking and/or stiffening of trunk and extremities, which can be readily observed by the clinician. Non-convulsive seizures can only be identified by the use of electroencephalography while convulsive seizures may or may not require electroencephalography to be identified.

In recent decades, the discovery of a high incidence and prevalence of convulsive and non-convulsive status epilepticus in critically ill patients has been well studied in adults and children. In addition to non-convulsive status epilepticus, a variety of abnormal brain patterns, which lie in range of the so-called ictal-interictal continuum, have been described. Although clinical effects of some of these abnormal brain patterns have been described in the literature, there remain a number of abnormal patterns of unknown clinical significance. Nonetheless, it is necessary to identify the presence of these patterns in order to adequately provide medical treatment and care. The gold standard method of identification of both normal and abnormal brain waves is electroencephalography, a technology well known in the art which makes use of a set of sensors/electrodes that are placed in contact with the scalp of a human or animal subject in order to capture the miniscule electrical signals produced by brain cells which are then processed and displayed for interpretation by a trained professional. By means of electroencephalography, brain waves can be classified into normal and abnormal, with varying degrees in between. Many specific abnormal brain patterns are known some of which include spike and waves, periodic discharges, rhythmic delta activity, among many others. Electroencephalography is well established as the most effective technology to characterize these patterns and in turn make clinical decisions.

Some abnormal brain wave patterns, such as those seen in non-convulsive status epilepticus, require emergency treatment, and failure to identify these patterns in a timely fashion can lead to irreversible brain damage and death. Due to the nature of electroencephalography (EEG) technology, often times there are delays in arriving at a diagnosis. EEG usually, but not always, involves a) a technician transporting EEG machines to the bedside; b) preparing the scalp of the patient with special gels; c) attaching a number of electrodes, usually 21, to the patient's scalp; d) recording the EEG; e) disconnecting the electrodes from the patient; f) transporting and uploading the EEG data to a server which can then be accessed and interpreted by a physician; g) communicating the results to other treating physicians. Due to this multi-step, complex process, delays in diagnosis ensue thereby translating into adverse patient outcomes. Furthermore, due to this complex endeavor, higher costs are implicit. Attempts to make this process more efficient have had varying degrees of failure and success. For example, methods to obtain "abbreviated EEG" information from only a limited number of electrodes ranging from 2 to 8 have been described but the results remain controversial with groups of clinicians finding some positive results while others discourage its use. Similarly using various electrode montage schemes which aim to make the process simpler and faster, such as the so-called "hairline montage," have been met with skepticism. Another alternative that has been tried is the use of special helmets, headbands, head strips, headsets and caps with special arrangements of electrodes which aim to make the acquisition of EEG signals simpler and faster, however with lack of widespread support by the physician community.

One modality, is the use of continuous EEG by which patients in intensive care units are connected to EEG for prolonged periods of time but this modality still has cost-related and logistical issues, some of which include:

a) Using this modality still requires a dedicated EEG technician and mounting anywhere from 8 to 21 electrodes on the patient's scalp.

b) After initial installation, the electrodes require frequent maintenance in order to prevent the appearance of artifacts, which would make the EEG recordings undecipherable.

Hence, it would be desirable to have an electroencephalography device that can provide an optimal-quality, safe, low-cost and efficient way of rapidly assessing the presence of abnormal electrical brain activity in emergency situations in which the current gold-standard electroencephalography technology and techniques (namely, continuous or beside 16-channel. EEG) are inadequate or simply not available in emergency situations. Furthermore, it would also be desirable to have a device that allows the Clinician the ability and flexibility of performing this assessment with the least possible delay in acquisition. Still further, it would be desirable to have a device that by allowing these freedoms to the Clinician, it also significantly improves the decision-making and outcome of an acute medical intervention. Therefore, there currently exists a need in the industry for a device and associated method that allows rapid evaluation of the presence of seizures and other electrical brain abnormalities in seriously ill patients in the intensive care unit and emergency department.

SUMMARY OF THE INVENTION

In one aspect, the present invention relates to a wearable mobile electroencephalography device comprising 1 a sensor element, 2 a fabric element, 3 a signal-processing element, 4 an analysis and display element, and 5 Cables and/or wireless transmission elements.

In a related aspect, the present invention relates to a method of assembling a wearable mobile electroencephalography device, the method comprising the steps of: attaching the sensor element in 1 to the fabric element or wearable element in 2, wherein said fabric or wearable element is capable of being mounted on a user's finger 10 or hand 15, wherein said sensor element 1, is operably connected or networked via cables 5 or wireless transmission elements 11 to a signal-processing element 3, and wherein said signal-processing element 3 is operably connected or networked via cables 5 or wireless transmission elements 11 to an analysis and display element 4.

In a related aspect, the present invention relates to a method of measuring electroencephalographic signals in a subject, the method comprising applying the sensor element 1 of the device of the present invention on a contact surface on said subject and obtaining a reading of the subject's brain wave patterns.

In another related aspect, the present invention relates to a method of diagnosing abnormal brain wave patterns in a subject, the method comprising applying the sensor element 1 of the device of the present invention on a contact surface on said subject and obtaining a reading of the subject's brain wave patterns.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. Copies of this patent or patent application publication with drawing(s) will be provided by the Office upon request and payment of the necessary fee.

DETAILED DESCRIPTION OF THE INVENTION

Figure 1:
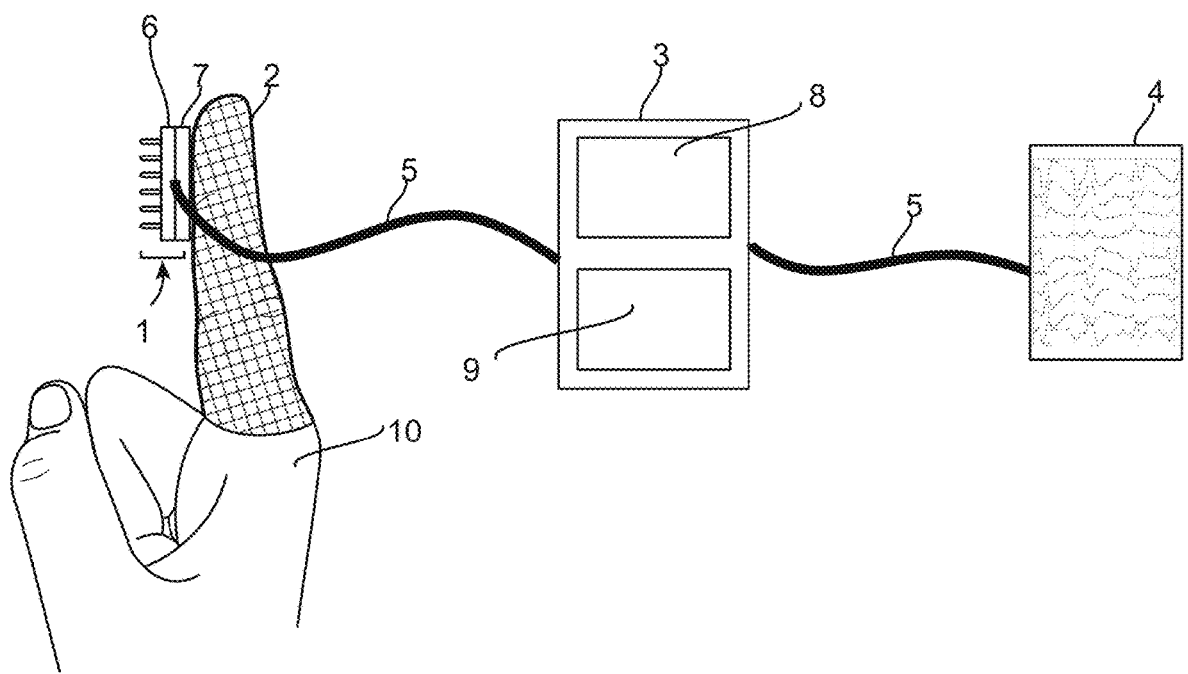
FIG. 1 shows the sensor element 1, attached to the fabric element 2. The sensor element 1 is connected to the signal-processing element 3 by cables 5. The signal-processing element is connected to the analysis and display element 4 by cables 5. The user's finger 10 is inserted into the fabric element 2. The sensor element 1 comprises the preamplifier component 7 and the electrode component 6. The signal-processing element 3 comprises an amplifier component 8 and an analog-to-digital component 9.

The term "signal source" used herein means the biological substrate that generates physiological electrical currents that can be recorded, processed and displayed as a waveform by means of electroencephalography.

The term "subject" used herein means a human or an animal.

The term "user" used herein means a person who employs the present invention for research or clinical purposes.

The term "contact surface" used herein means the area or body part of a subject which any device, component or sensor of the present invention touches in order to sense or detect a signal source. For example, in one embodiment the contact surface is the scalp of a subject. In another embodiment, the contact surface is the meninges of a subject. In another embodiment, the contact surface is the brain of a subject. In another embodiment, the contact surface is the skin over the face of a subject. As such, many other contact surface embodiments may come to mind to those skilled in the arts.

The distinction between signal source and contact surface is necessary because physiological electrical currents generated by neuronal tissue of humans or animals may be recorded, sensed or detected by the present invention at sites in close proximity or distant from the signal source. For example, if the signal source is the brain tissue of the subject, a sensor element (see definition below) may be placed over the scalp in order to record the electrical currents that are generated by the brain, traversing several layers of tissue, which include the meninges, fat, bone and skin to finally arrive at the contact surface.

The term "sensor element" used herein means any device, component or sensor that detects a signal source at the contact surface of a subject. For example, in one embodiment, the sensor element is placed over the human scalp where it detects the electrochemical currents generated by neuronal tissue. In one embodiment, the sensor element can perform diverse processes such as amplification, filtering and transduction of said electrochemical currents.

The term "fabric element" used herein means a cloth, weaved or knitted, that can be fitted into the hands or fingers of the user. In one embodiment the fabric element is a glove. In another embodiment the fabric element is a finger cot.

The term "preamplifier component" used herein means any device, component or sensor that receives an electrical signal, performs transformation or manipulation of said signal and sends the transformed signal to other electronic components for further processing.

The term "electrode component" used herein means any device, component or sensor that touches the contact surface and transduces into electrical signals the electrochemical signals generated by the signal source.

In one embodiment, the present invention relates to a wearable mobile electroencephalography device comprising 1 a sensor element, 2 a fabric element, 3 a signal-processing element, 4 an analysis and display element, and 5 cables and/or 11 wireless transmission elements.

In another embodiment, the present invention relates to a method of assembling a wearable mobile electroencephalography device, the method comprising the steps of: a) attaching the sensor element in 1 to the fabric element or wearable element in 2, wherein said fabric or wearable element is capable of being mounted on a users' finger or hand, wherein said sensor element 1, is operably connected or networked via cables 5 or wireless transmission elements 11 to a signal-processing element 3, and wherein said signal-processing element 3 is operably connected or networked via cables 5 or wireless transmission elements 11 to an analysis and display element 4.

In one embodiment, the present invention relates to a method of measuring electroencephalographic signals in a subject, the method comprising applying the sensor element 1 of the device of the present invention on a contact surface on said subject and obtaining a reading of the subject's brain wave patterns.

In another embodiment, the present invention relates to a method of diagnosing abnormal brain wave patterns in a subject, the method comprising applying the sensor element 1 of the device of the present invention on a contact surface on said subject and obtaining a reading of the subject's brain wave patterns.

Figure 2:
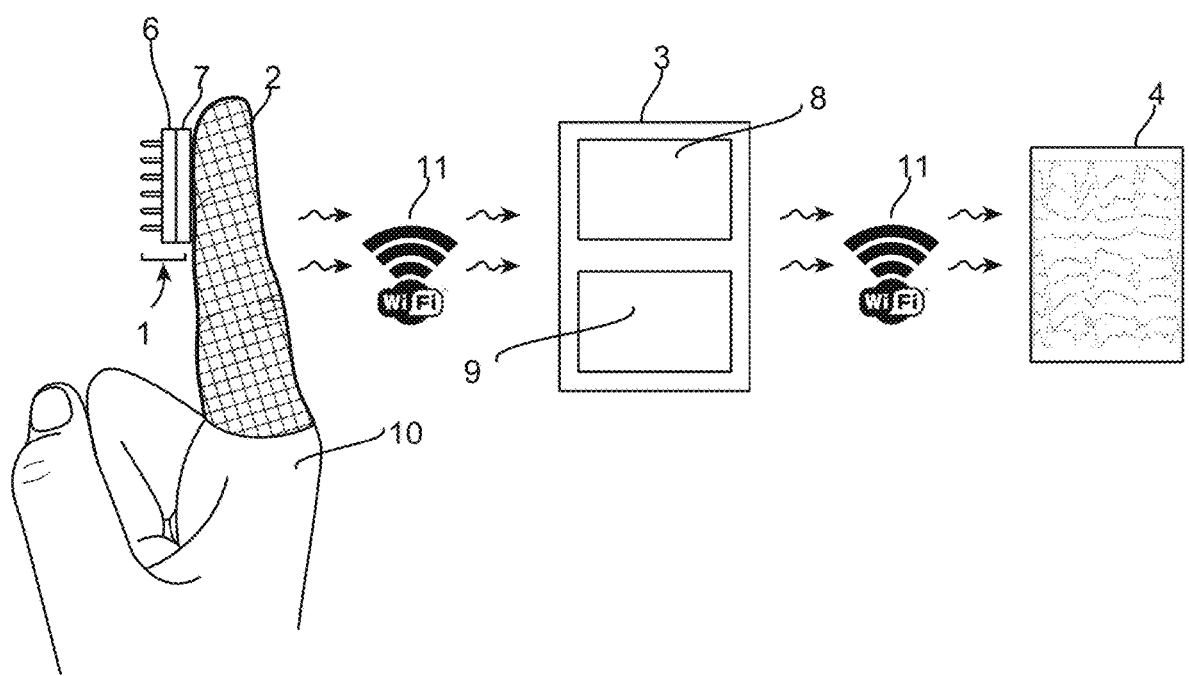
FIG. 2 shows the sensor element 1, attached to the fabric element 2. The sensor element 1 is networked to the signal-processing element 3 by wireless WiFi communication 11. The signal-processing element 3 is networked to the analysis and display element 4 by wireless WiFi communication 11. The user's finger 10 is inserted into the fabric element 2. The sensor element 1 comprises the preamplifier component 7 and the electrode component 6. The signal-processing element 3 comprises an amplifier component 8 and an analog-to-digital component 9.

The present invention is a wearable electroencephalography device that is attached to the user's hands and/or fingers. In its most complete form, and as shown in FIG. 1 and FIG. 2, the present invention comprises the following elements: A sensor element 1 comprising an electrode component 6 and a preamplifier component 7; A fabric element 2 which fits snugly into the user's hand and/or fingers 10; A signal-processing element 3 comprising an amplifier component 8 and an analog-to-digital conversion component 9; An analysis and display element 4; cables 5 or wireless transmission 11 that connect or network the different elements of the invention.

FIG. 2 shows an embodiment of the present invention, which uses wireless communication (WiFi) 11 to transmit information between the different elements. FIG. 2 shows the other elements of the invention as follows: sensor element 1 comprising a preamplifier component 7 and an electrode component 6; A fabric element 2 which fits snugly into the user's hand and/or fingers 10; A signal-processing element 3 comprising an amplifier component 8 and an analog-to-digital converter component 9; An analysis and display element 4.

Figure 3:
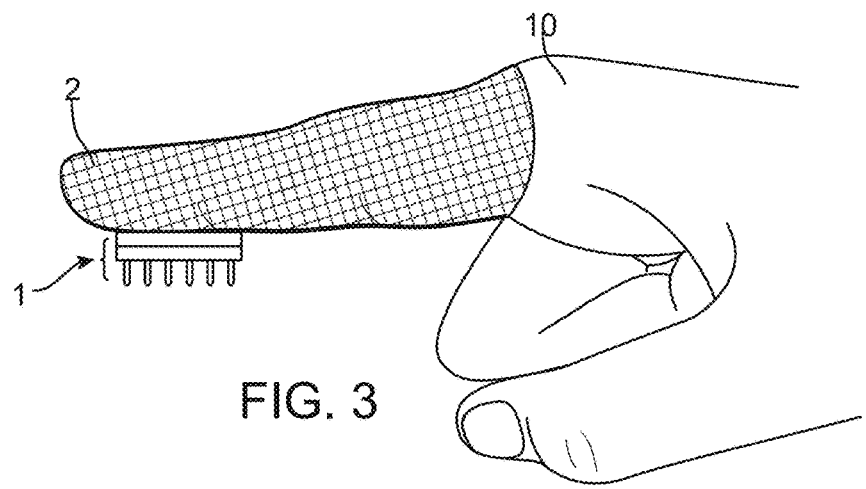
FIG. 3 shows the user's finger 10 inserted into the fabric element 2. The sensor element 1 is attached to the fabric element 2.
Figure 4:
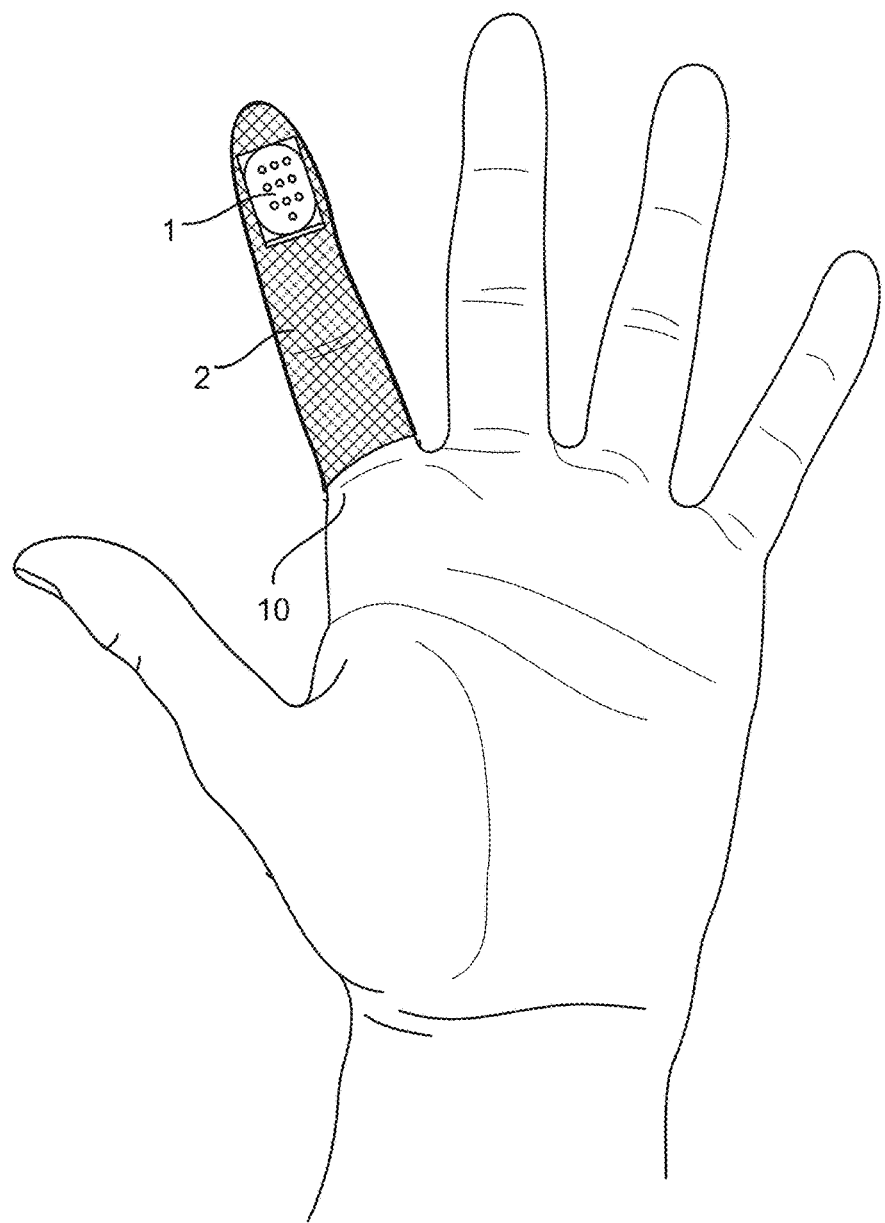
FIG. 4 shows the user's finger 10 inserted into the fabric element 2. The sensor element 1 is attached to the fabric element 2.

In one embodiment, as shown in FIG. 3 and FIG. 4, the fabric element 2 is shown as a finger cot, which fits snugly in the user's index finger 10. The sensor element 1 is attached to the fabric element 2 by sutures. In another embodiment, Velcro attaches the sensor element 1 to the fabric element 2. In yet another embodiment, glue attaches the sensor element 1 to the fabric element 2. Other embodiments may employ any combination of glue, Velcro and sutures to attach the sensor element 1 to the fabric element 2.

Figure 5:
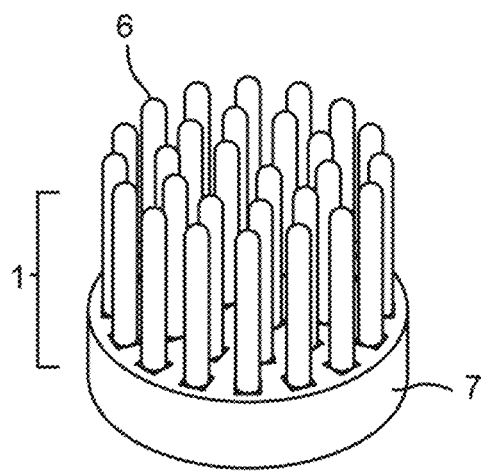
FIG. 5 shows the electrode component 6 and the preamplifier component 7 of the sensor element 1.
Figure 6:
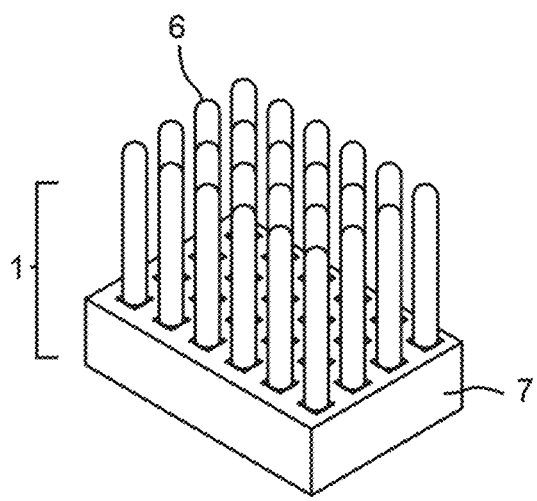
FIG. 6 shows the electrode component 6 and the preamplifier component 7 of the sensor element 1.

FIG. 5 and FIG. 6 show embodiments of the sensor element 1 comprising a preamplifier component 7 and an electrode component 6, which are electrically connected. In one embodiment, the electrode component 6 comprises a number of blunt metal needles arranged in a square grid and soldered onto a rectangular metal plate within the preamplifier component 7. In another embodiment the electrode component 6 comprises a number of blunt metal needles arranged in concentric circles and soldered onto a circular metal plate within the preamplifier component 7. In another embodiment, the electrode component 6 comprises a number of blunt needles made of conductive plastic arranged in a square grid and directly fused to a rectangular conductive plastic base within the preamplifier component 7 by the method of injection molding known in the arts. In another embodiment, the electrode component 6 comprises a number of blunt needles made of conductive plastic arranged in concentric circles and directly fused to a circular conductive plastic base within the preamplifier component 7 by the method of injection molding known in the arts. In another embodiment the electrode component comprises a flat square metal plate. In another embodiment the electrode component comprises a flat circular metal plate. In another embodiment the electrode component comprises a circular metal plate with a convex side that touches the contact surface.

It is worth clarifying that the sensor element implemented in this invention is known in the electroencephalography (EEG) scientific literature as a "dry active electrode". This is in contrast to the traditional "passive electrodes" which are the gold standard. By "dry" what is meant is that a conductive paste is not required at the skin-electrode interface in order to enhance the transduction of the electrochemical signals generated by the signal source. By "active" what is meant is that the electrode is directly connected to electronic circuitry that is able to perform limited pre-processing and manipulation of the transduced signal. The "active" component is herein referred to as the preamplifier component of the sensor element. These features implemented in the sensor element confer this invention several key advantages over the traditional "passive electrodes" used in traditional EEG. First of all, it significantly cuts the time required to apply the sensor element over the contact surface by: a) Not having to scrub the contact surface with abrasive pastes and b) Not having to apply a conductive paste to enhance transduction. Second, it improves the quality of signal acquisition by pre-amplifying the signal source right at the contact surface thus decreasing a common source of artifact in traditional EEG-cable movement artifact. These features are highly desirable in emergency clinical situations in which speed and quality are of utmost concern.

Figure 7:
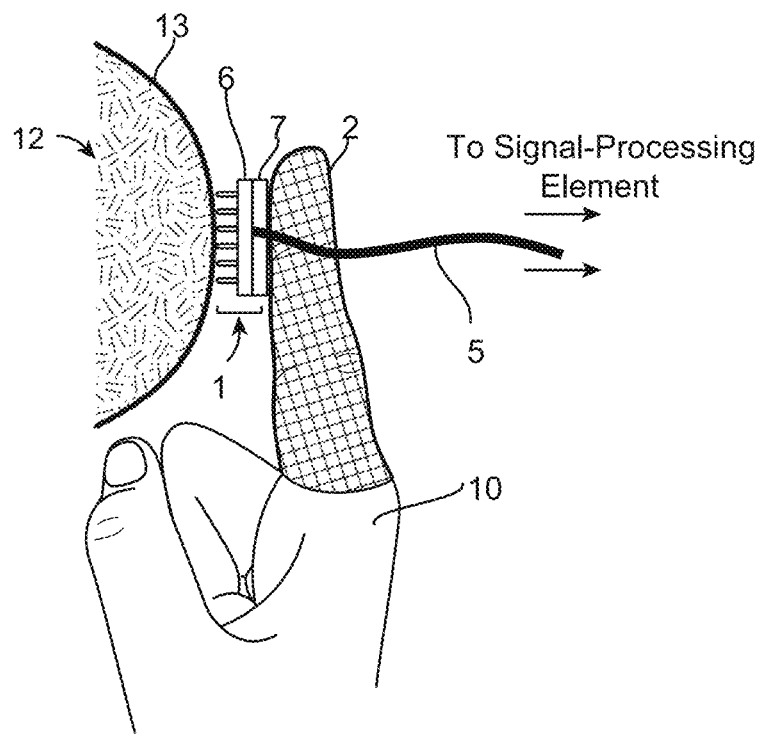
FIG. 7 shows the sensor element 1 is touching the contact surface 13 of the signal source 12. The sensor element 1 is attached to the fabric element 2 and a cable 5 is seen connected to the sensor element 1. The user's finger 10 is inserted into the fabric element 2. The sensor element 1 comprises the electrode component 6 and the preamplifier component 7.

In one embodiment shown in FIG. 7, the sensor element 1, comprising an electrode component 6 and a preamplifier component 7, is attached to the fabric element 2 which is snugly fitted to the index finger 10 of the user. A cable 5 connected to the sensor element 1 transmits the signal acquired from the signal source 12 to the signal-processing element (not shown in this figure).

Figure 8:
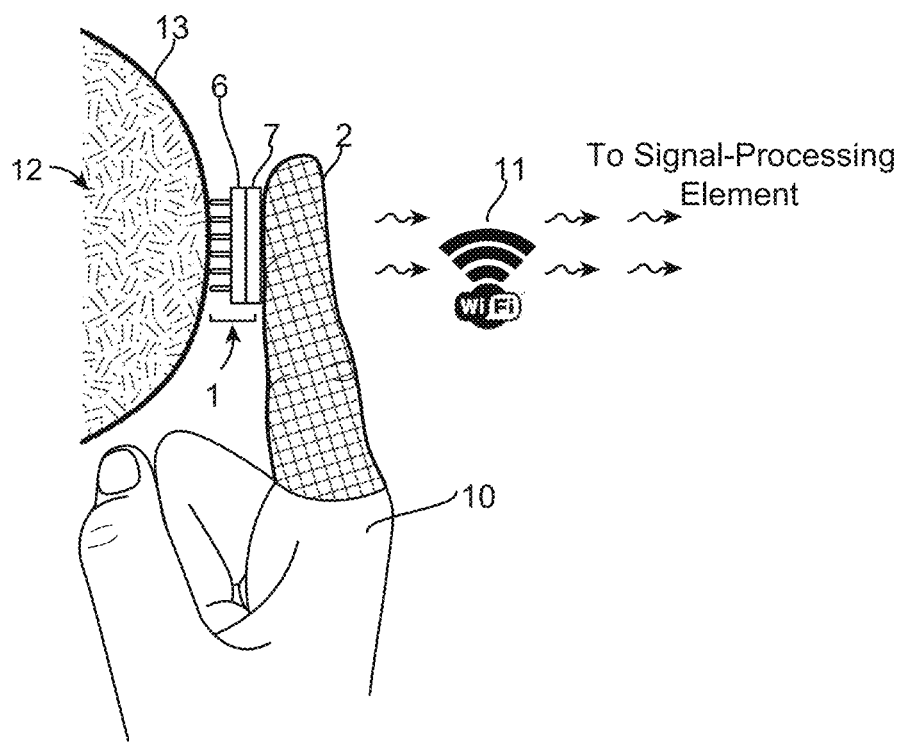
FIG. 8 shows the sensor element 1 is touching the contact surface 13 of the signal source 12. The sensor element 1 is attached to the fabric element 2 and a wireless device 11 is seen networking to the sensor element 1. The user's finger 10 is inserted into the fabric element 2. The sensor element 1 comprises the electrode component 6 and the preamplifier component 7.

In one embodiment shown in FIG. 8, the sensor element 1, comprising an electrode component 6 and a preamplifier component 7, is attached to the fabric element 2 which is snugly fitted to the index finger 10 of the user. The signal acquired by the sensor element 1 is transmitted to signal-processing element (not shown in this figure) by means of wireless transmission 11. Note that in this embodiment, the electrode component 6 of the sensor element 1 is touching the contact surface 13. The signal source 12 is also shown in this figure. The figure also shows an embodiment of the electrode component 6 comprising an array of blunt metal needles soldered onto a flat metal plate or circuit board within the preamplifier component 7.

Figure 9:
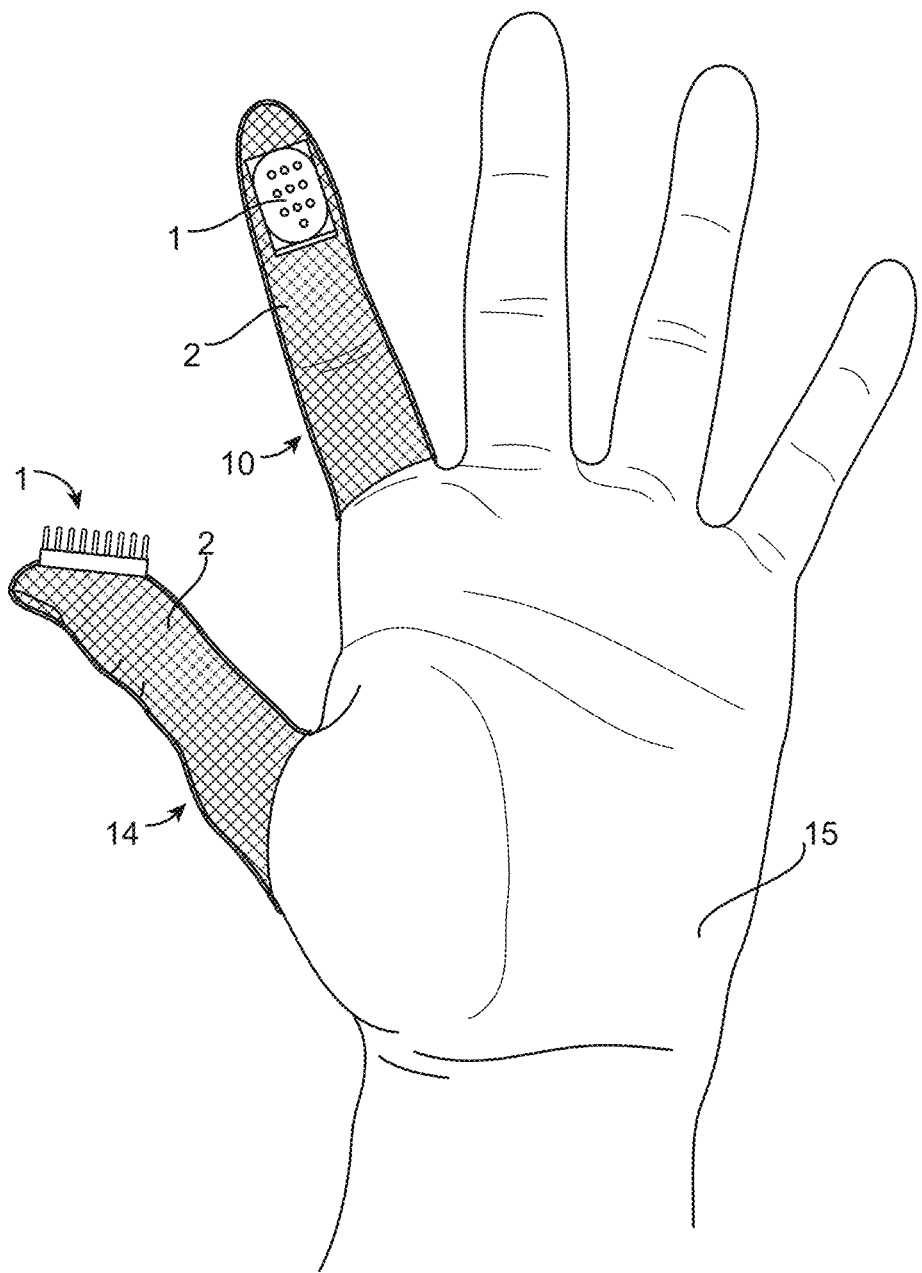
FIG. 9 shows the sensor element 1 attached to the fabric element 2. The thumb 14 and index 10 fingers and the palm of the user's hand 15.

In one embodiment shown in FIG. 9, the left hand of the user is in supine position with the palm of the hand 15 visible. Fabric elements 2 are therein embodied as finger cots that snugly fit the thumb 14 and index finger 10. Sensor elements 1 are attached to each of the fabric elements 2.

Figure 10:
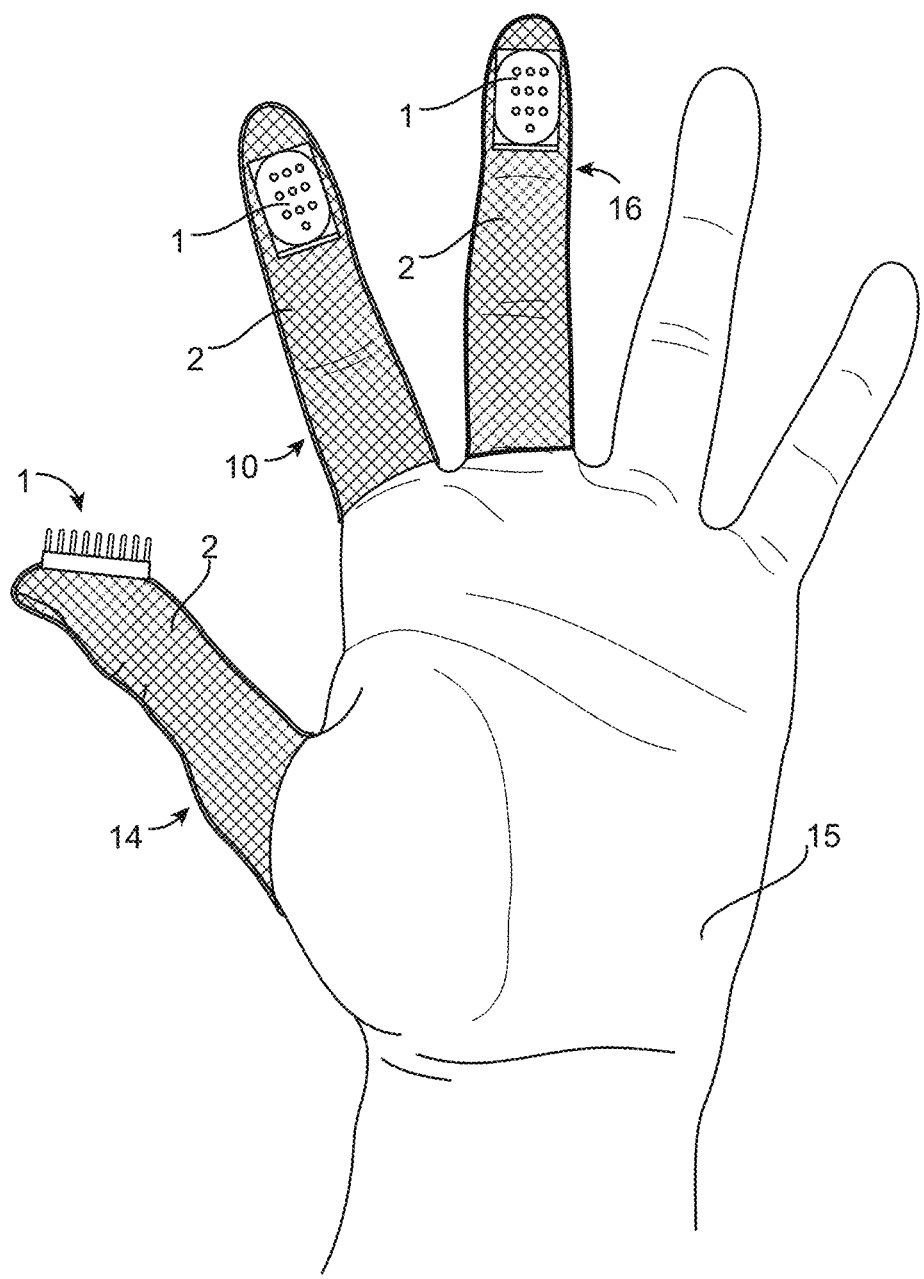
FIG. 10 shows the sensor element 1 attached to the fabric element 2. The thumb 14, index finger 10, third digit 16 and the palm of the user's hand 15.

In one embodiment shown in FIG. 10, the left hand of the user is in supine position with the palm of the hand 15 visible. Fabric elements 2 are therein embodied as finger cots that snugly fit the thumb 14, index finger 10 and third digit 16. Sensor elements 1 are attached to each of the fabric elements 2.

Figure 11:
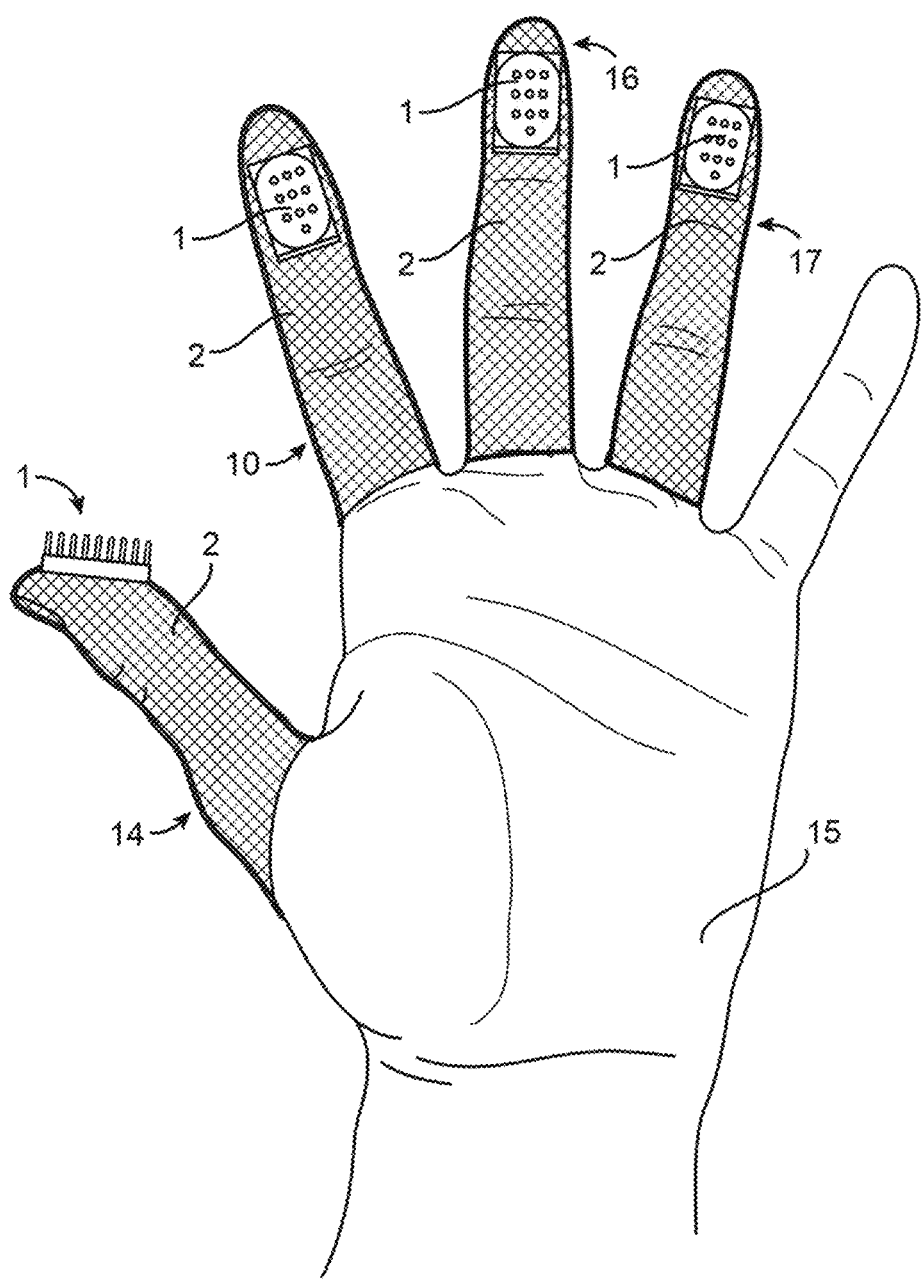
FIG. 11 shows the sensor element 1 attached to the fabric element 2. The thumb 14, index finger 10, third digit 16, fourth digit 17 and the palm of the user's hand 15.

In one embodiment shown in FIG. 11, the left hand of the user is in supine position with the palm of the hand 15 visible. Fabric elements 2 are therein embodied as finger cots that snugly fit the thumb 14, index finger 10, third digit 16 and fourth digit 17. Sensor elements 1 are attached to each of the fabric elements 2.

Figure 12:
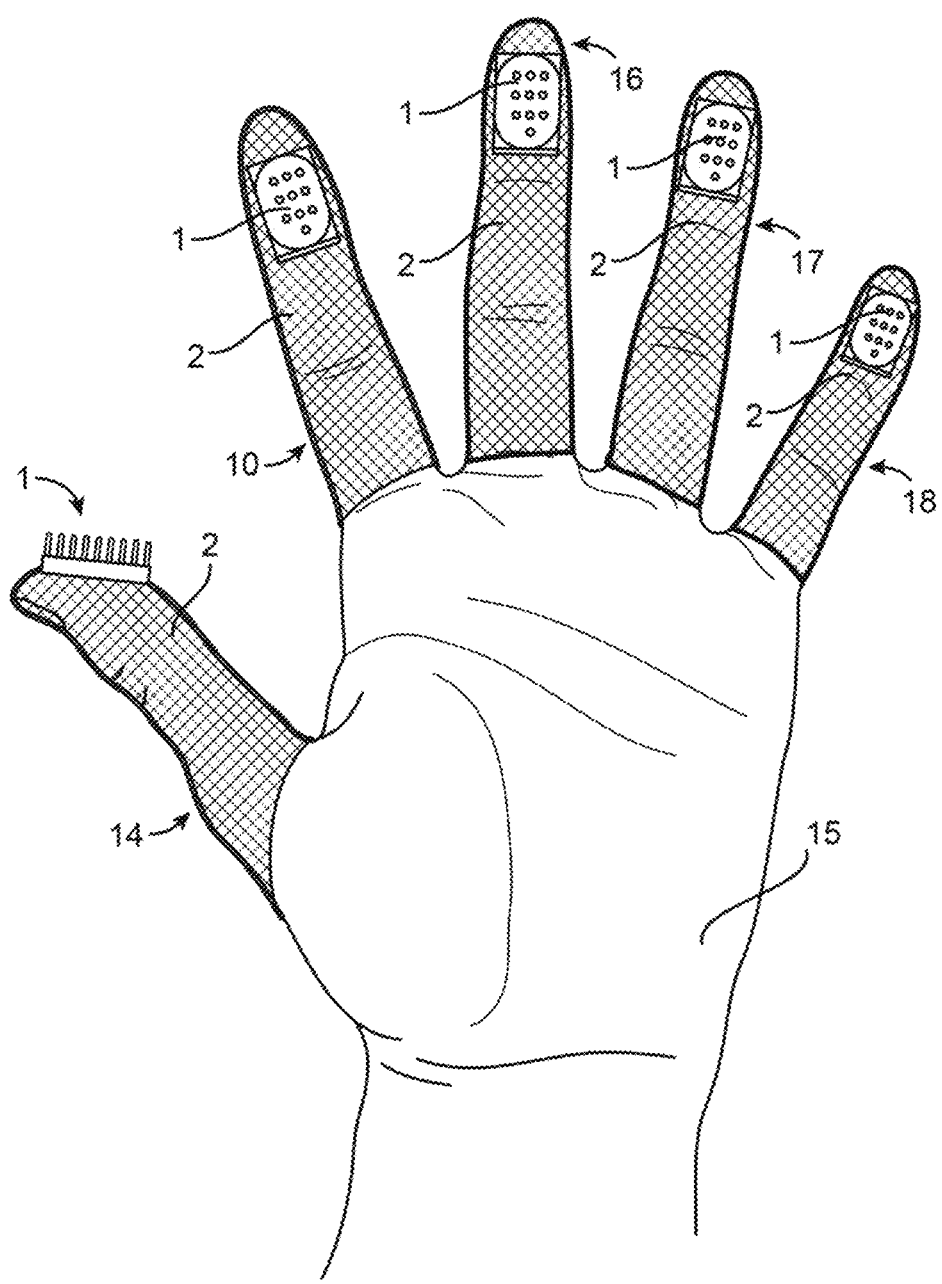
FIG. 12 shows the sensor element 1 attached to the fabric element 2. The thumb 14, index finger 10, third digit 16, fourth digit 17, fifth digit 18 and the palm of the user's hand 15.

In one embodiment shown in FIG. 12, the left hand of the user is in supine position with the palm of the hand 15 visible. Fabric elements 2 are therein embodied as finger cots that snugly fit the thumb 14, index finger 10, third digit 16, fourth digit 17 and fifth digit 18. Sensor elements 1 are attached to each of the fabric elements 2.

Figure 13:
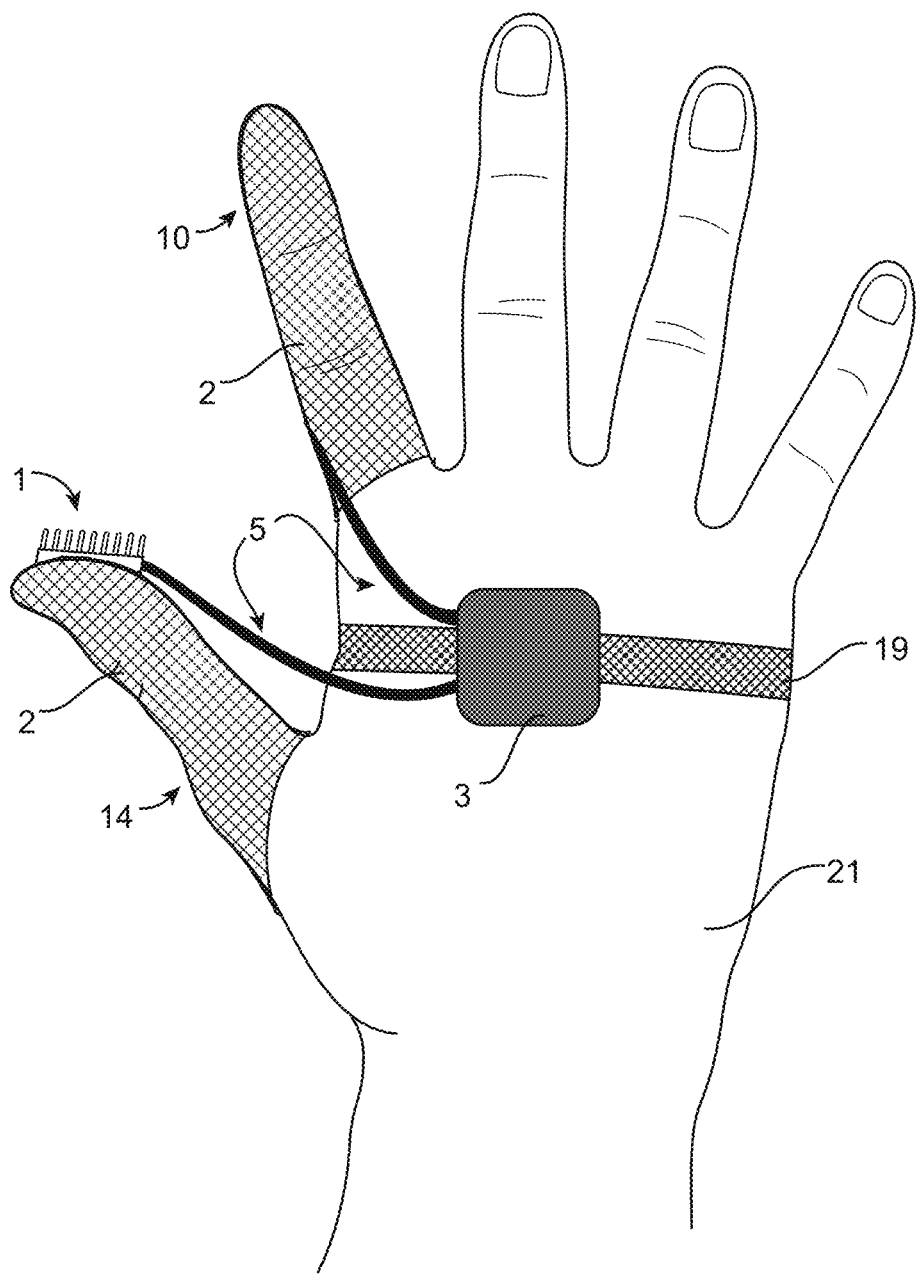
FIG. 13 shows the sensor element 1 attached to the fabric element 2. The user's thumb 14 and index fingers 10 are inserted into the fabric element 2. The sensor element 1 is connected to the signal-processing element 3 by cables 5. The signal-processing element 3 is affixed to the dorsum of the user's hand 21 by means of an elastic strap 19.

FIG. 13 shows an embodiment of the invention in which the right hand of the user is in prone position with the dorsum of the hand 21 visible. In this embodiment, the signal-processing element 3 is strapped to the dorsum of the hand 21 with an elastic strap 19 that wraps around the hand. A cable 5 connects a sensor element 1 to the signal-processing element 3. A second cable 5 is visible going from the signal-processing element 3 towards the palmar side of the index finger 10 where a sensor element is attached as seen in FIG. 14.

Figure 14:
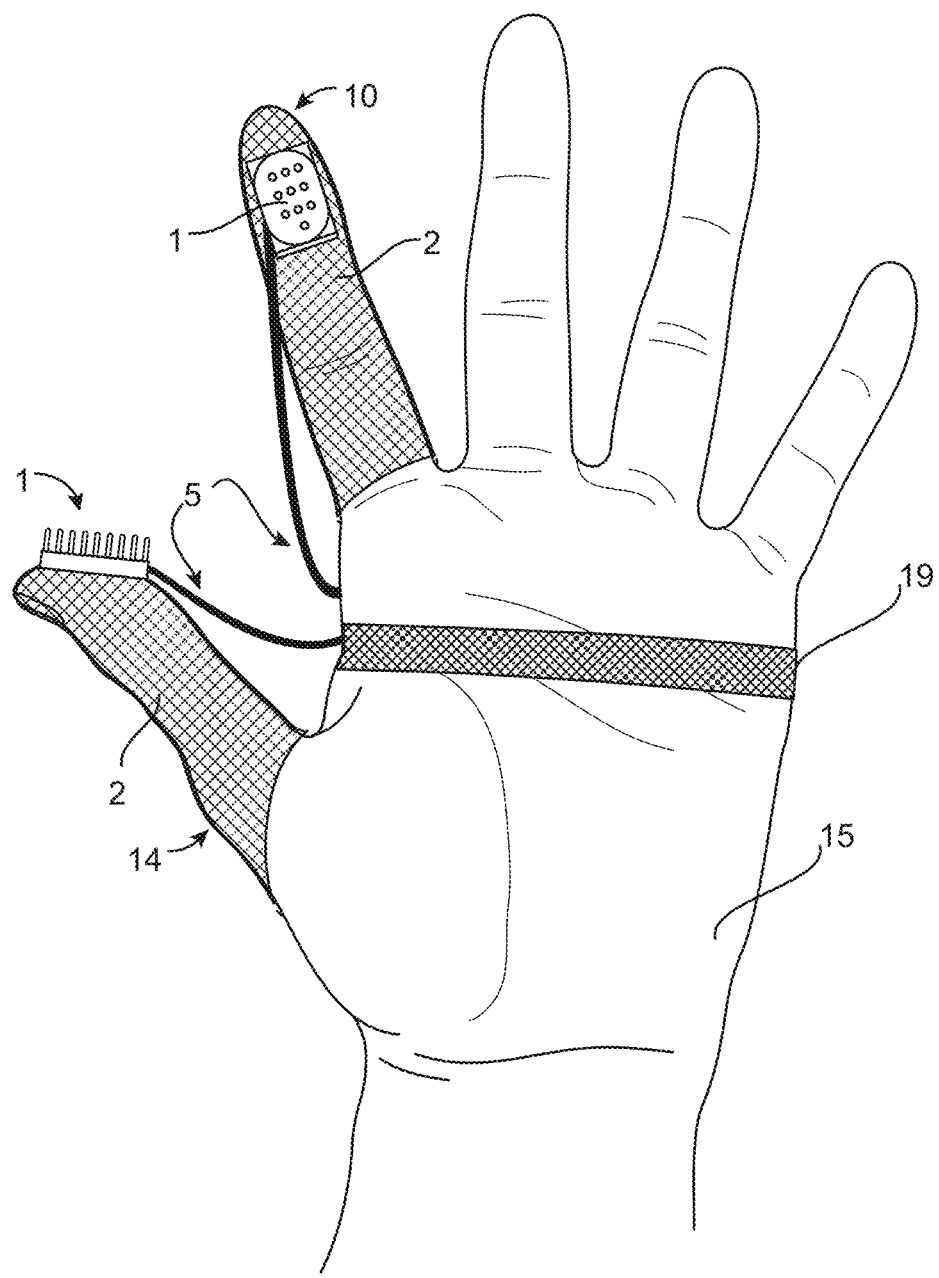
FIG. 14 shows the sensor element 1 attached to the fabric element 2. The user's thumb 14 and index fingers 10 are inserted into the fabric element 2. Cables 5 are seen going from the sensor element 1 towards the dorsum of the user's hand to connect with the signal-processing element (not shown). An elastic strap 19 wraps around the user's hand to affix the signal-processing element.

FIG. 14 shows the left hand of the user in supine position with the palm of the hand 15 visible. This figure shows an embodiment wherein sensor elements 1 are attached to fabric elements 2 inserted into the thumb 14 and index fingers 10 of the user's left hand. Cables 5 are seen connecting the sensor elements 1 and wrapping around to the dorsum of the hand to the signal-processing element as seen in FIG. 13. An elastic strap 19 affixes the signal-processing element 3 (FIG. 13) to the hand.

Figure 15:
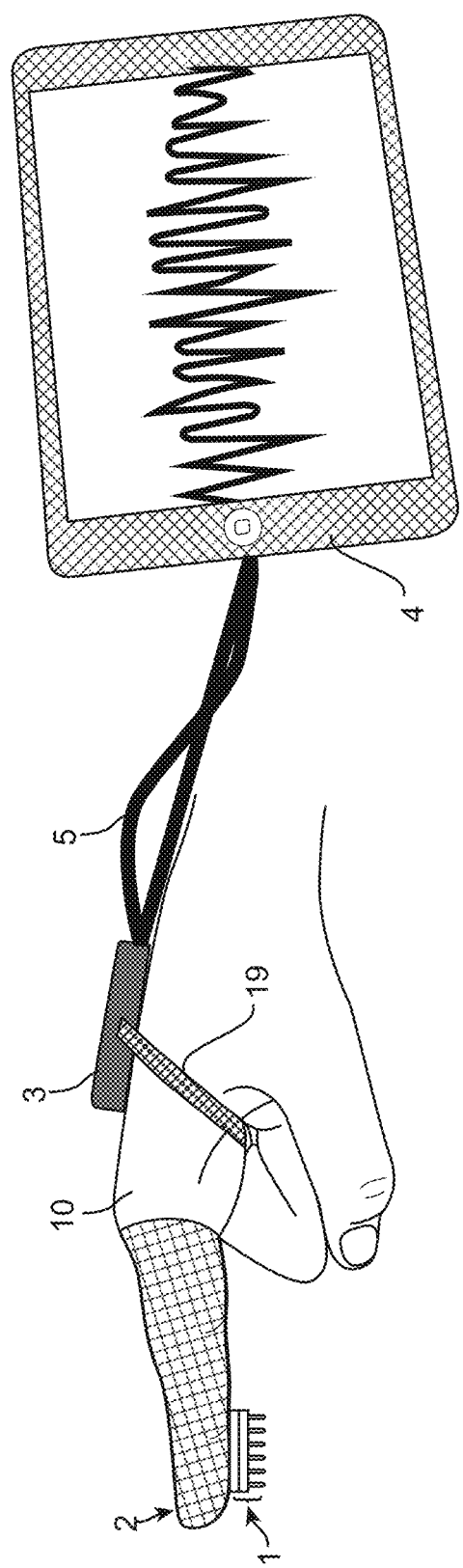
FIG. 15 shows the sensor element 1 attached to the fabric element 2. Cables 5 connect the signal-processing element 3 with the analysis and display element 4. The signal-processing element 3 is affixed to the user's hand by an elastic strap 19 that wraps around the user's hand.
Figure 16:
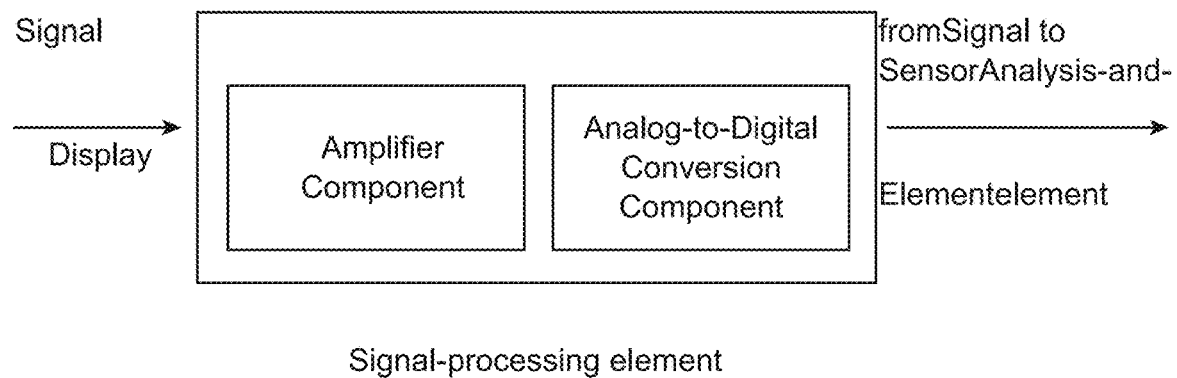
FIG. 16 shows a schematic diagram of the signal-processing element 3 comprising an amplifier component 8 and an analog-to-digital component 9.
Figure 17:
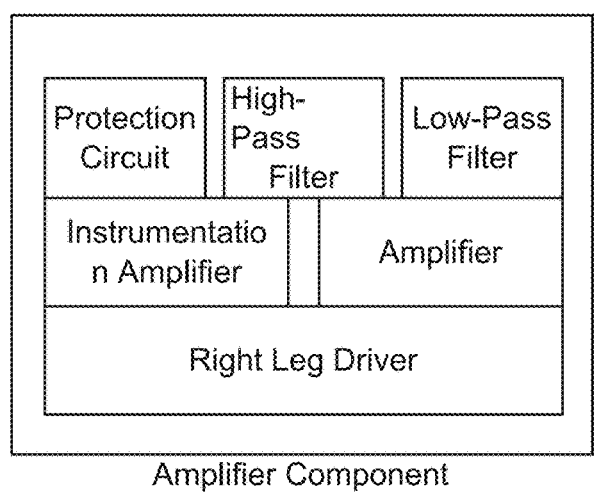
FIG. 17 shows a schematic diagram of the amplifier component.
Figure 18:
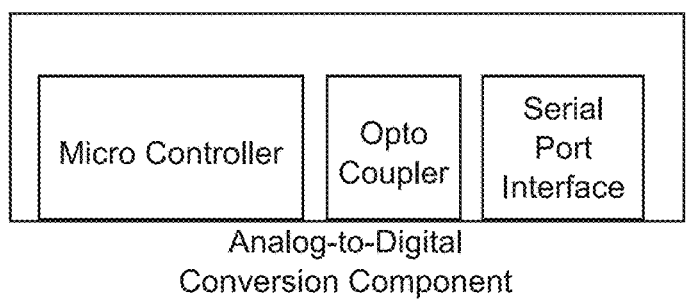
FIG. 18 shows a schematic diagram of the analog-to-digital conversion component.
Figure 19:
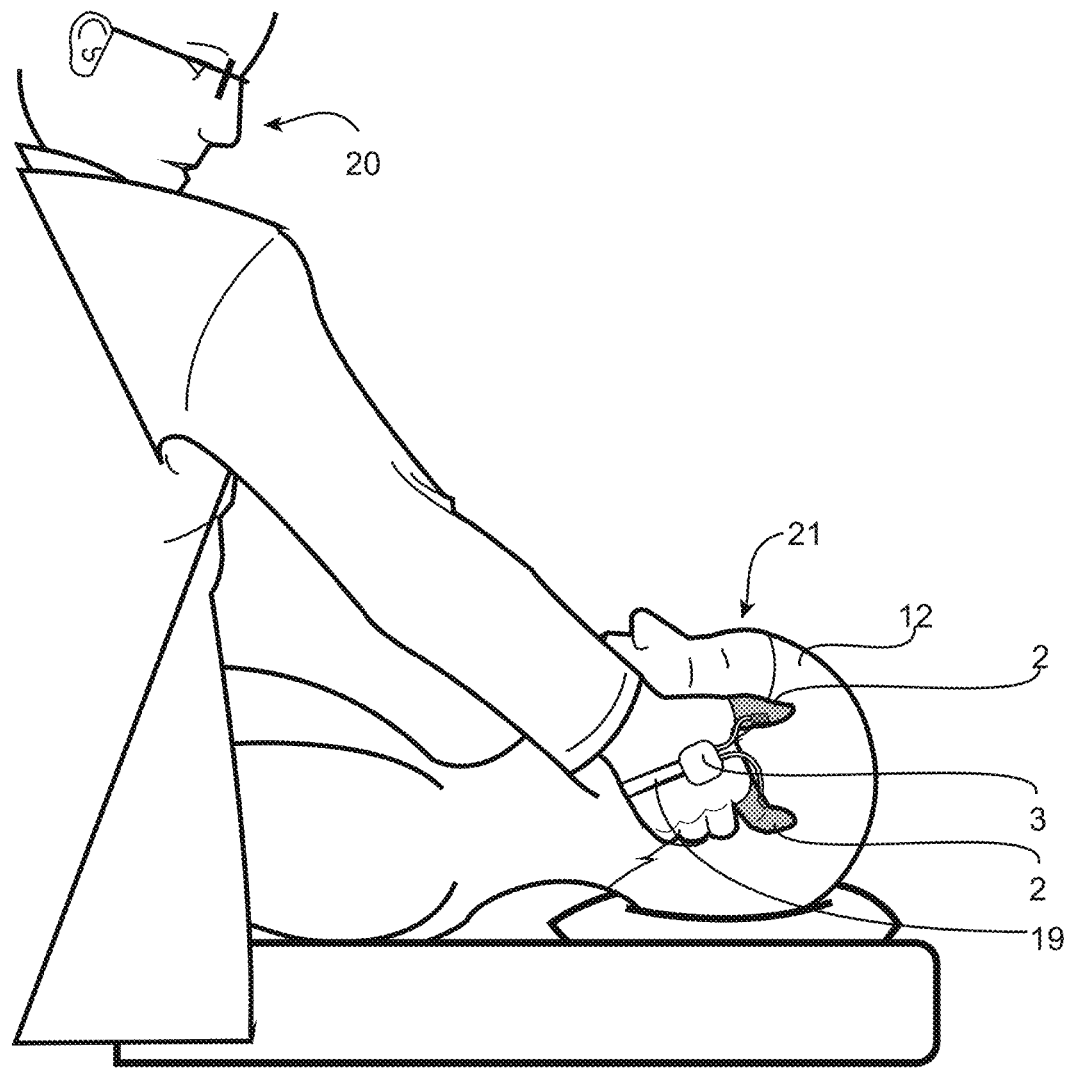
FIG. 19 shows the user 20 performing an electroencephalogram on the subject 21. The user is wearing the fabric element 2 on his thumb and index fingers. The signal-processing element 3 is affixed to the user's hand by an elastic strap 19. The fabric element 2 with the attached sensor element (not shown in this graphic) is touching the contact surface of the signal source 12, which is the subject's scalp in this embodiment.
Figure 20:
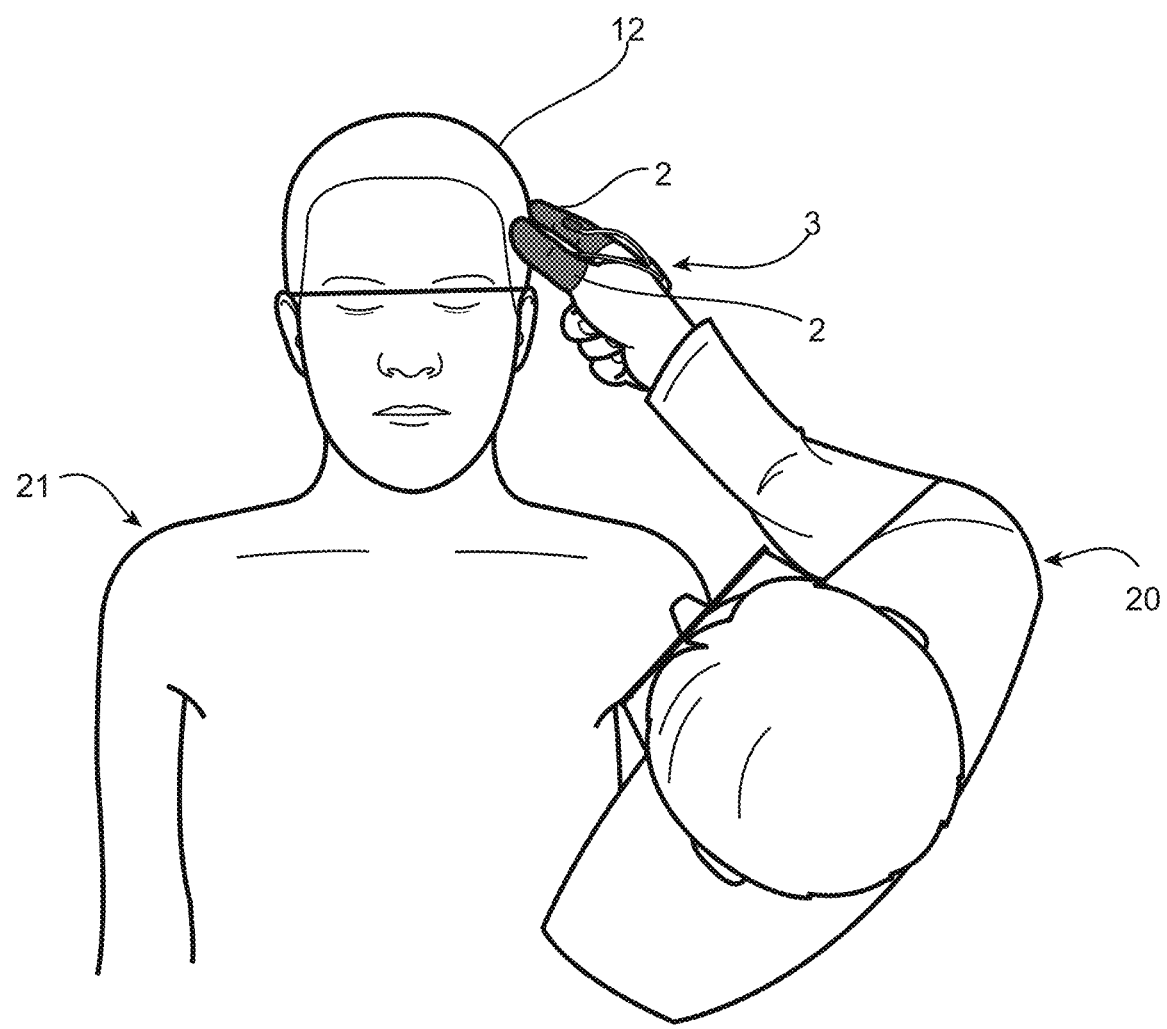
FIG. 20 shows the user 20 performing an electroencephalogram on the subject 21. The user 20 is wearing the fabric element 2 on his thumb and index fingers. The signal-processing element 3 is affixed to the user's hand by an elastic strap (not shown in this graphic). The fabric element 2 with the attached sensor element (not shown in this graphic) is touching the contact surface of the signal source 12, which is the subject's scalp in this embodiment.
Figure 21:
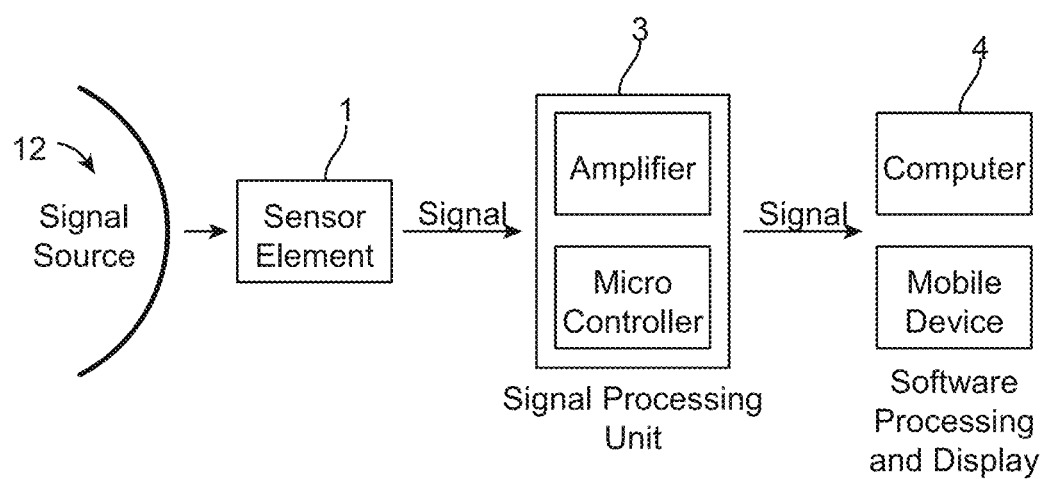
FIG. 21 shows a simplified schematic and flow diagram showing the different elements of the invention and the process by which a brain wave signal is acquired, processed and displayed. From left to right, the image shows a schematic representation of the signal source 12; a schematic representation of the sensor element 1; a schematic representation of the signal-processing element 3 and its components in one embodiment; a schematic representation of a desktop computer or mobile device which are two possible embodiments of the analysis and display element 4 of the invention.

FIG. 15 shows an embodiment of the invention with a fabric element 2 inserted onto the user's right index finger 10. An embodiment of the sensor element 1 is attached to the fabric element 2. In this embodiment, the signal-processing element 3 is strapped to the hand by means of an elastic strap 19. In this embodiment, a cable 5 is seen connecting the signal-processing element 3 to an embodiment of the analysis and display element 4.

In one embodiment of this invention the analysis and display element is a mobile device such as a tablet. In another embodiment the analysis and display element is a different type of mobile device, a smart phone. In yet another embodiment, the analysis and display element is a laptop computer. In yet another embodiment, the analysis and display element is a desktop computer.

In one embodiment, the present invention is used in emergency clinical situations in which critically ill patients are suspected of having seizures and it accomplishes its task by allowing the medical practitioner or technician, herein also referred to as the user, to insert in his/her hand and/or fingers a fabric element with a number of sensor elements which can then be maneuvered freely to come in contact with the patient's scalp or cortex. Once the sensor element is in contact with the patient's body part of interest, the brain signals are preamplified and buffered by the sensor element. The signals are then transmitted to a signal-processing element, which amplifies, filters and converts the analog signals to digital signals. The signal is then transmitted to an analysis and display element for further digital processing and visual display of the signal.

In a preferred embodiment the present invention overcomes the clinical, technical, financial and logistical limitations that traditional electroencephalography poses when a patient who is critically ill in the emergency department or intensive care unit is suspected of having seizures or abnormal electrical brain patterns that could potentially result in irreversible brain damage. The conventional devices and methods of electroencephalography follow the paradigm of attaching a number of electrodes, which are usually passive (as understood by experts in the arts), directly on the patient's scalp at fixed locations after a process of preparing each site by abrasion and application of conductive gels wherever an electrode needs to be placed. Traditionally, the preparation process requires a technician to use an abrasive/conductive paste to interface skin and electrode. The process is time-consuming, labor-intensive and logistically difficult which poses significant challenges in emergency situations. Furthermore, the traditional paradigm mandates that the electrodes be attached to the patient's scalp following a standardized electrode placement system.

In one embodiment the present invention provides the unexpected advantage that it is actually worn by the user, which in one embodiment is a clinician. This is in sharp contrast to the traditional methods of electroencephalography in which the electrodes are placed directly over the scalp of the patient.

In one embodiment the present invention provides the unexpected advantage that it does not require time-consuming skin preparation.

In one embodiment the present invention provides the unexpected advantage that it allows significant flexibility by allowing the examiner to maneuver the sensor elements freely to areas of interest on the body part of interest.

In one embodiment the present invention provides the unexpected advantage that ensuing examination can result in better decision-making by the user in a more timely and efficient manner. This is highly desirable in emergency situations in which patients are suspected of having seizures.

With respect to the associated method, and in one embodiment, in order to carry out the method of the present invention the following steps are followed:
1) The user 20 identifies a medical necessity.
2) The user 20 proceeds to insert his own hand and/or fingers into the fabric element 2, wherein said fabric element 2 is attached to a sensor element 1.
3) The user 20 maneuvers his fingers to come into contact with a subject's 21 contact surface 12, which in another embodiment is the scalp. In another embodiment, the contact surface is the subject's head. In another embodiment, the contact surface is the subject's cerebral cortex.
4) The user 20 reviews in real-time the signals generated.
5) The user 20 detects and diagnoses abnormal brain wave patterns by visualizing said patterns on an analysis and display element 4.

In one embodiment, at the conclusion of these steps, the digital data collected by the device and analyzed by software allows the user to make informed decisions in real-time and in emergency situations regarding the further management of the patient.

While the present invention has been described above in terms of specific embodiments, it is to be understood that the invention is not limited to these disclosed embodiments. Many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. A method of using an electroencephalography (EEG) device in a diagnostic manner on a subject, comprising:
   providing a finger element for releasably mounting on one or more fingers of a user;
   providing a sensor element on the finger element,
      the sensor element being releasably applicable by the mounted finger element to at least a subject separate from the user,
      the sensor element having at least an electrode for sensing EEG signals from the subject,
      the sensor element being unapplied from the separate subject after sensing the EEG signals,
      the finger element remaining mounted on the one or more fingers of the user as the sensor element is being unapplied from the separate subject after sensing the EEG signals, and
      the sensor element including at least a preamplifier component for processing the sensed EEG signals;
   providing a signal-processing element apart from the finger element and operably connected to the sensor element for processing the sensed EEG signals received from the sensor element; and
   providing an analysis and display element apart from the finger element and operably connected to the signal-processing element for receiving processed sensed EEG signals from the signal-processing element, for analyzing the processed sensed EEG signals, and for displaying analysis results.

2. An electroencephalography (EEG) system for serial use in a diagnostic manner with a user only having to releasably mount a finger element in at least a finger to releasably touch the finger element of the EEG system to a separate subject to obtain results for the separate subject, and with the user being able to move on from the separate subject to touch another separate subject with the finger element remaining mounted on the at least finger of the user to obtain results for the another separate subject, and so on, comprising:
  a finger element for releasably mounting on at least a finger of a user;
  the finger element including a sensor element releasably applicable to a separate subject by the user moving the finger element so the sensor element contacts the separate subject,
  the sensor element being releasably applied to the separate subject,
  the finger element remaining mounted on the at least finger of the user when the sensor element is releasably applied to the separate subject,
    the sensor element sensing EEG signals from the separate subject, and
    the sensor element being unapplied from the separate subject by the user moving the mounted finger element away from the separate subject;
  the sensor element including a preamplifier component operably connected to the sensor element for processing the EEG signals from the separate subject;
  an analysis and display element being operably connected to the sensor element of the finger element for receiving the EEG signals from the separate subject, for analyzing the EEG signals from the separate subject, and for displaying analysis results for the separate subject; and
  the finger element being further operable by remaining mounted on the at least finger of the user to releasably apply the sensor element to another separate subject to sense EEG signals from the another separate subject, and to provide the EEG signals from the another separate subject to the analysis and display element for analysis of the EEG signals from the separate another subject and display of the analysis results for the separate another subject.

3. The EEG system of claim 2, further comprising:
a preamplifier component included on the sensor element of the finger element for processing the EEG signals and providing the processed EEG signals to the analysis and display element with the analysis and display element being operable to analyze the processed EEG signals.

4. The EEG system of claim 2, further comprising:
a signal-processing element being operably connected to the sensor element of the finger element for signal-processing the EEG signals and providing the signal-processed EEG signals to the analysis and display element with the analysis and display element being operable to analyze the signal-processed EEG signals.

5. The EEG system of claim 2, further comprising:
a preamplifier component included on a sensor element for processing EEG signals and providing the processed EEG signals to a signal-processing element,
the preamplifier element being operably connected to the sensor element; and
the signal-processing element being operably connected to the preamplifier component for signal-processing the processed EEG signals and providing the signal-processed EEG signals to an analysis and display element with the analysis and display element being operable to analyze the signal-processed EEG signals.

6. A device for use as part of an electroencephalography (EEG) system to obtain a set of EEG signals, respectively, from one or more subjects, comprising:
  a sleeve configured for releasably mounting on one or more fingers of a user and including a sensor element for sensing a set of EEG signals from a separate subject;
  the sleeve being configured to remain mounted on the one or more fingers of the user to releasably touch the separate subject for the sensor element to sense the set of EEG signals of the separate subject, and after sensing the set of EEG signals, the sleeve being movable away from contact with the separate subject by remaining mounted on the one or more fingers of the user;
  the sleeve including communication means for providing the set of EEG signals from the separate subject to an EEG system for analysis of the set of EEG signals; and
  the mounted sleeve on the one or more fingers of the user being movable to releasably touch another separate subject for the sensor element to sense a set of EEG signals of the another separate subject, to process the set of EEG signals from the another separate subject; and to provide the EEG signals from the another separate subject to the EEG system for analysis.

7. The device of claim 6, further comprising:
a preamplifier on the sleeve for processing the set of EEG signals from the separate subject and for transmitting the processed set of EEG signals through the communications means to the EEG system for analysis.

8. The device of claim 7, wherein the preamplifier processes the set of EEG signals by pre-amplifying the set of EEG signals to decrease artifact in the set of EEG signals.

9. The device of claim 6, wherein the sensor element is disposed on the sleeve so that when the sleeve is mounted on one or more fingers of the user, the sensor element is mounted on the top underside of the sleeve in a position adjacent palm side of the one or more fingers of the user.

10. The device of claim 6, wherein the sensor element comprises at least a dry electrode.

11. The device of claim 6, wherein the sensor element senses the set of EEG signals without application of a conductive paste on the subject.

12. The device of claim 6, wherein the sleeve is movable by remaining mounted on the one or more fingers of the user to releasably touch a first surface of the separate subject for the sensor element to sense the set of EEG signals of the separate subject, and the sleeve being movable away from the first surface of the separate subject to a second surface of the separate subject to sense a second set of EEG signals of the separate subject by remaining mounted on the one or more fingers of the user.

13. The device of claim 6, further comprising:
a signal-processor connected to the sensor of the sleeve for signal-processing the set of EEG signals and providing the signal-processed set of EEG signals to the EEG system for analysis.

14. The device of claim 6, further comprising:
a preamplifier on the sleeve for processing the set of EEG signals and providing the processed set of EEG signals to a signal-processor connected to the sleeve; and
the signal-processor being operable to signal-process the processed set of EEG signals and provide the signal-processed set of EEG signals to the EEG system for analysis.

* * * * *